United States Patent [19]

Hanrahan et al.

[11] Patent Number: 5,349,958
[45] Date of Patent: Sep. 27, 1994

[54] METHOD AND DEVICE FOR CUTANEOUS MARKING OF THE VENOUS ANATOMY

[75] Inventors: Lawrence M. Hanrahan, Austin, Tex.; Lawrence P. Kinney, Cincinnati, Ohio

[73] Assignee: Core Medical Technologies, Inc., Houston, Tex.

[21] Appl. No.: 60,870

[22] Filed: May 13, 1993

Related U.S. Application Data

[62] Division of Ser. No. 851,032, Mar. 12, 1992, Pat. No. 5,226,419.

[51] Int. Cl.$^5$ .............................................. A61B 8/00
[52] U.S. Cl. ........................ 128/660.01; 222/402.19
[58] Field of Search ...................... 128/662.04, 661.09, 128/660.01; 222/402.19, 402.24

[56] References Cited

U.S. PATENT DOCUMENTS

| | | | |
|---|---|---|---|
| 3,810,459 | 5/1974 | Becker | 128/662.04 |
| 4,127,842 | 11/1978 | Hassler | 128/661.09 |
| 4,978,038 | 12/1990 | Sullivan | 222/402.19 |

*Primary Examiner*—George Manuel
*Attorney, Agent, or Firm*—Jones, Day, Reavis & Pogue

[57] ABSTRACT

A device (10) and method for cutaneously marking the venous anatomy with an ink. The method comprises selectively locating a portion of the venous anatomy to be marked and coating the skin (20) corresponding to the venous anatomy to be marked with a transmission gel (22). The transmission gel (22) permits a technician utilizing an ultrasound transducer to pinpoint the portion of the venous anatomy to be marked. Device (10) simultaneously clears the transmission gel from the skin (20) corresponding to the portion of the venous anatomy to be marked and marks the open space (24) on the skin (20) with the ink.

14 Claims, 1 Drawing Sheet

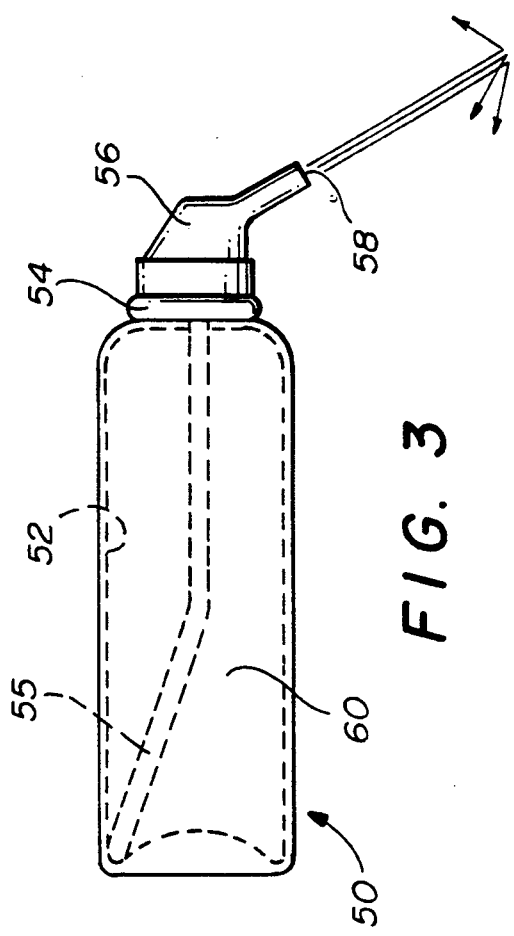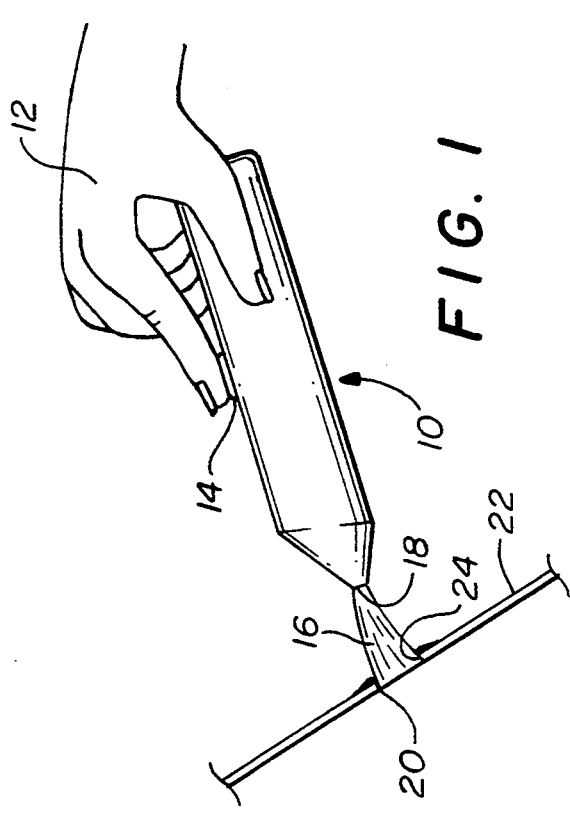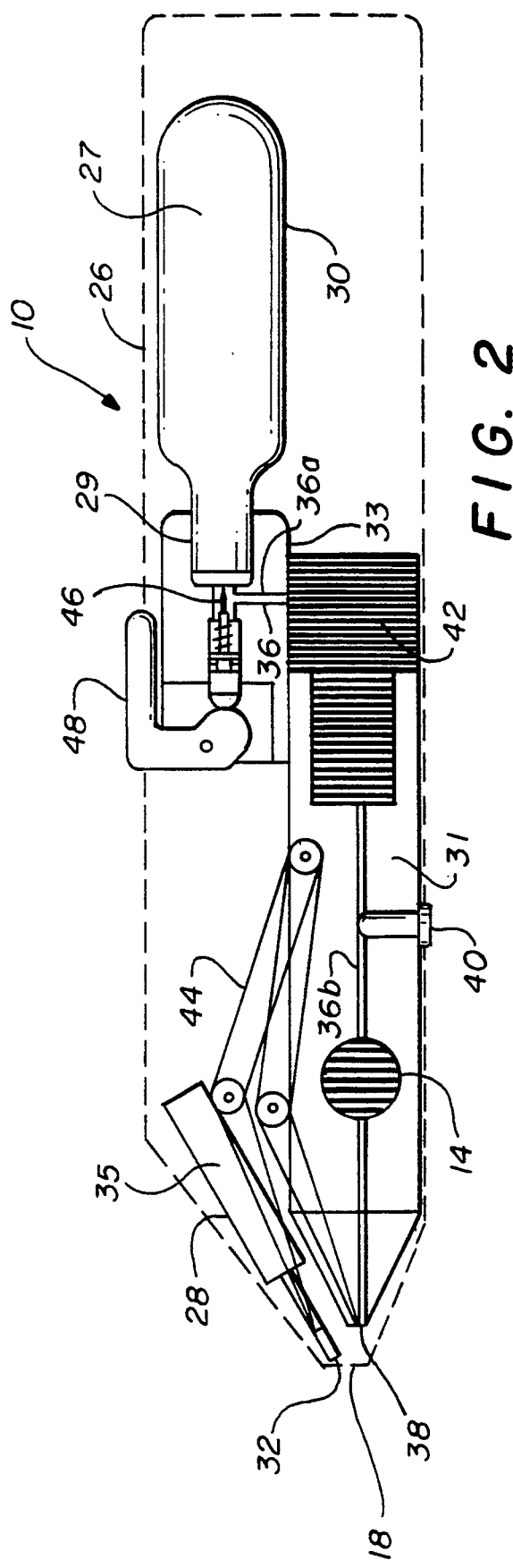

METHOD AND DEVICE FOR CUTANEOUS MARKING OF THE VENOUS ANATOMY

CROSS REFERENCE TO RELATED APPLICATION

This is a division of application Ser. No. 07/851,032 filed Nov. 13, 1992 now U.S. Pat. No. 5,226,419.

TECHNICAL FIELD OF THE INVENTION

This invention relates in general to a device and method for marking the anatomy, and in particular to a device and method for cutaneously marking the venous anatomy of a human being prior to surgery.

BACKGROUND OF THE INVENTION

Venous diseases reportedly affect between 500,000 and 1,000,000 persons per year. Venous diseases affect a much younger age group than heart or lung diseases, or most cancers. Due to their chronic nature, the diseases remove people in the prime of their earning potential from the work-force. The resulting cost to society is enormous. Past efforts to improve the quality of life, let alone restore work-force capacity, for affected persons have been difficult as discussed in J Mayberry, G Moneta, L Taylor, J Porter, Nonoperative Treatment of Venous Stasis Ulcer, *Venous Disorders*, 1991.

Within the last ten years there has been a renewed interest in the study of venous diseases by both physicians and scientists. This interest can generally be attributed to the application of ultrasound imaging techniques to the study of venous diseases.

To assist a vascular surgeon, it is desirable to evaluate a patient's venous anatomy prior to an operation. To further assist the surgeon, it is desirable to create a "map" of the underlying venous anatomy on the relevant area of the patient's skin. Currently, there are two procedures available to accomplish these tasks. The first is an invasive technique called a venogram. The procedure involves injecting a radioactive dye into the patient's veins and then taking an x-ray of the relevant area. The anatomy is visualized on the x-ray film, thus providing the surgeon with evaluative material, but no marks can be accurately placed on the patient's skin from the technique. Moreover, because of its invasive nature, a venogram creates a risk of adverse effects to the patient.

The second procedure currently used is a non-invasive technique that utilizes ultrasound imaging equipment and a conventional ink marker. The ultrasound equipment requires a transmission gel to be spread on the patient's skin to fill the air space between the skin's surface and the surface of the ultrasound transducer. The transducer transmits and receives ultrasound pulses to and from the patient's tissue. The presence of the transmission gel, however, prevents a mark from being directly placed on the patient's skin. As a result, the procedure requires two technicians; one technician operates the ultrasound transducer while the other technician wipes away the transmission gel and marks the skin corresponding to the underlying venous anatomy with the ink marker. A further drawback of the procedure is that it does not allow for a continuously connected line to be marked on the limb of a patient. Rather, marking occurs at two inch intervals over the length of a limb resulting in a line of dots. Only after the dotted line has been marked and the limb wiped clean of the transmission gel can the dots be connected to form a continuous line. Thus, the currently used non-invasive method is cumbersome, time-consuming and expensive because of the necessity of utilizing two technicians. As a result, "mapping", although desirable, is often an unemployed tool.

The present invention addresses the problems associated with the currently used methods by providing a non-invasive efficient transfer of clinical information from the ultrasound technician to the vascular surgeon. The present invention requires only one ultrasound technician to "map" the venous anatomy of a patient. The invention eliminates the need to first wipe away the layer of transmission gel required to operate the ultrasound transducer before marking the area of skin corresponding to the underlying venous anatomy. In addition, the ink used in the present invention is quick-drying and water insoluble, and, therefore, is not disturbed by the ultrasound transmissions gel. As a result, the present invention leaves an ink mark on the patient's skin which will remain for several days until the surgical procedure can be carried out. Being non-invasive, the invention also does not pose an independent risk to a patient. Therefore, the present invention provides a safe, quick and efficient method for "mapping" the venous anatomy of a patient that will aid the vascular surgeon.

SUMMARY OF THE INVENTION

The present invention involves a device and method for cutaneously marking the venous anatomy of a patient in preparation for surgery.

One embodiment of the device has the appearance of a large marker. A plastic encasing covers the interior components of the device. Inside the encasing, a housing provides an inlet port for a propellent source, and an outlet port for discharge of the pressurized gas contained in the propellent source. A channel connects the inlet port to the outlet port. The flow of pressurized gas through the channel is controlled by a regulator, which reduces the initial pressure of the gas from the propellent source, and a switch, which prevents or allows the pressurized gas to proceed through the channel to the outlet port. The switch is located on the exterior of the plastic encasing. In addition, a pressure control located on the exterior of the plastic encasing provides for additional regulation of the pressure of the gas as it travels through the channel toward the outlet port. A reservoir containing the marking fluid is affixed to the housing. The opening in the reservoir is directed at an angle between approximately 30° and approximately 60° to the horizontal center axis of the device. The outlet port of the channel and the opening in the reservoir come in close proximity at the orifice which is located at one end of the plastic encasing.

Initially, the device is made operative by engaging the piercing assembly located at the inlet port. Pulling a lever that is on the exterior of the plastic encasing causes a piercing needle to penetrate the seal of the propellent source. Pressurized gas released from the propellent source returns the lever to its original position. Once released, the gas enters the channel and proceeds to the regulator. The regulator reduces the pressure of the gas. Depressing the switch opens the channel to allow the pressurized gas to proceed to the outlet port. The initial burst of pressurized gas that occurs immediately upon depressing the switch disperses the ultrasound transmission gel present on the patient's skin.

In addition, upon exiting the outlet port the pressurized gas passes the opening in the reservoir thereby drawing the marking fluid out of the reservoir and atomizing it upon discharge (the Venturi effect). The mixture of pressurized gas and marking fluid exit the orifice of the plastic encasing and proceed to clear the transmission gel from, and, simultaneously, leave an ink mark on, the patient's skin. Both the pressurized gas and the marking fluid are water insoluble, and, therefore, neither combines with the water soluble ultrasound transmission gel. As a result, the quick-drying marking fluid remains on the skin even after the transmission gel is removed.

Another embodiment of the device utilizes a conventional aerosol can as its housing. The chamber within the can contains a mixture of the pressurized gas and the marking fluid. A channel connects the chamber to an inlet port. An actuator plugs into the inlet port. The actuator has a spout which is directed at an angle between approximately 30° and approximately 60° from the vertical center axis the can. Depressing the actuator causes the mixture of pressurized gas and marking fluid to flow through the channel and to discharge through the spout. Again, the initial burst disperses the transmission gel allowing the marking fluid to make an ink mark on the patient's skin.

The method for cutaneously marking the venous anatomy involves one ultrasound technician utilizing an ultrasound transducer in conjunction with one of the above disclosed embodiments. The technician first generally locates the relevant portion of the venous anatomy to be marked, and coats the skin corresponding to that area with ultrasound transmission gel. The transmission gel permits the ultrasound transducer to produce an image of the underlying venous anatomy on a television monitor so that the technician can pinpoint the portion of the venous anatomy to be marked. Utilizing one of the embodiments disclosed above, the technician is then able to simultaneously clear the transmission gel from the skin that corresponds to the portion of the venous anatomy to be marked, and mark the open space on the skin with a quick-drying, water insoluble ink. As a result of the ink used, the mark remains on the patient's skin even after the rest of the transmission gel is wiped off.

DESCRIPTION OF THE DRAWINGS

Other aspects of the present invention and their advantages may be appreciated with reference to the following Detailed Description of the Invention taken in conjunction with the appended Drawings in which:

FIG. 1 is a perspective view of the invention as seen in its environment;

FIG. 2 is a cross-sectional view of the invention; and

FIG. 3 is a cross-sectional view of an alternative embodiment of the invention.

DETAILED DESCRIPTION OF THE INTERVENTION

FIG. 1 is a perspective view of the present invention and is generally designated 10. Device 10 is held in a technician's hand 12. Device 10 is activated by depressing a switch 14. Once activated, device 10 discharges a spray 16 from an orifice 18. Spray 16 clears a layer of transmission gel 22 from an area of skin 20 thereby creating an open space 24 on skin 20. Simultaneously, spray 16 which comprises a quick-drying ink leaves a mark at open space 24.

FIG. 2 is a cross-sectional view depicting the preferred embodiment of the present invention. A plastic encasing 26 forms the exterior of device 10. In the preferred embodiment, plastic casing 26 is made of Lexan HPS, an FDA compliant polycarbonate resin. A housing 31 has an inlet port 33 at its first end and an outlet port 38 at its second end. A propellent source 30 is threadably engageable with threads 29 located in inlet port 33. Initially, to render device 10 operable, a lever 48 located on the exterior of plastic encasing 26 is pulled. Pulling lever 48 causes a piercing needle 46 to penetrate a seal (not shown) on propellent source 30. Lever 48 returns to its original position when a pressurized gas 27 is initially discharged from propellent source 30. Upon discharge from propellent source 30, pressurized gas 27 enters a first segment 36a of a channel 36 and thereafter flows into a regulator 42.

While propellent source 30 contains any conventional pressurized gas, in the preferred embodiment pressurized gas 27 is a mixture of between approximately 80% and approximately 90% 1.1-diflouroethane and between approximately 10% and approximately 20% butane by volume. In addition, the initial pressure of pressurized gas 27 while in propellent source 30 is between approximately 200 and approximately 300 pounds per square inch (psi). Regulator 42 is made of porous material with baffles. In the preferred embodiment, the porous material is composed of alternating slices of a porous non-rigid material and a porous rigid material to prevent clogging and provide volume as understood by one skilled in the art. Regulator 42 reduces the pressure of pressurized gas 27 to between approximately 10 and approximately 50 psi. Upon exiting regulator 42, pressurized gas 27 flows through a second segment 36b of channel 36 toward outlet port 38. Switch 14 controls the flow of pressurized gas 27 to outlet port 38. In addition, a pressure control 40 located on the exterior of plastic encasing 26 increases or decreases the diameter of channel 36 thereby decreasing or increasing the pressure of pressurized gas 27 in segment 36b of channel 36 downstream toward outlet port 38.

A reservoir 28 containing a marking fluid 35 is affixed to housing 31 by a fastener 44 which permits reservoir 28 to be moved within plastic encasing 26. Reservoir 28 has an opening 32 from which marking fluid 35 is discharged. In the preferred embodiment, fastener 44 is adjusted so that opening 32 is directed at an angle between approximately 30° and approximately 60° to the horizontal center axis of device 10. While marking fluid 35 contained in reservoir 28 can be any quick-drying, water insoluble ink, in the preferred embodiment the ink is combined with between approximately 80% and approximately 92% xylene by weight. Opening 32 and outlet port 38 come into close proximity at orifice 18.

Referring momentarily to FIG. 1 in conjunction with FIG. 2, device 10 is activated by pressing switch 14. A brief (1–2 second) burst of pressurized gas 27 is initially released, followed by a steady flow of the gas. The initial burst disperses transmission gel 22 located on skin 20. The flow of pressurized gas 27 past opening 32 in reservoir 28 draws out and atomizes marking fluid 35, more commonly referred to as the Venturi effect. Because marking fluid 35 and pressurized gas 27 are both water insoluble, spray 16 does not mix with transmission gel 22 which is water soluble. As a result, marking fluid 35 creates an ink mark at open space 24 on skin 20 which remains even after transmission gel 22 has been wiped away.

FIG. 3 is a cross-sectional view depicting the alternative embodiment of the present invention. An aerosol can 50 houses a chamber 52 which contains a mixture of pressurized gas and marking fluid 60. Aerosol can 50 may be any conventional aerosol can, but, in its preferred embodiment, is made of aluminum. The pressurized gas and marking fluid are the same as disclosed above. Mixture 60 is maintained in chamber 52 at a pressure of between approximately 10 and approximately 50 psi. Aerosol can 50 has a channel 55 inside chamber 52 which joins chamber 52 to an inlet port 54. An actuator 56 is affixed to inlet port 54. Actuator 56 has a spout 58 through which mixture 60 is discharged. Spout 58 is preferably directed at an angle between approximately 30° and approximately 60° from the vertical center axis of aerosol can 50. An optional feature of aerosol can 50 is a gas control (not shown) located on actuator 56 to control the pressure of mixture 60.

OPERATION

The present invention anticipates a device and method for cutaneously marking the venous anatomy of a human being with a quick-drying, water insoluable ink in preparation for surgery.

The present invention can be best understood by referring to FIGS. 1 and 2 simultaneously. The method for cutaneously marking the venous anatomy requires only one ultrasound technician. The technician first identifies the general area of the patient's venous anatomy to be marked, for example, the anterio-medial aspect of the right leg. The area of skin is then coated with ultrasound transmission gel. The transmission gel is a conductive material necessary for the ultrasound transducer to be able to produce an image of the underlying venous anatomy of, for example, the right leg. The image is viewed on a television monitor as the ultrasound transducer is manipulated over the gel. With the ultrasound equipment, the technician is able to pinpoint the underlying venous anatomy to be marked. Because the ultrasound transducer can be operated with one hand, the technician's other hand is free to utilize one of the embodiments of the present invention.

Following the path of the ultrasound transducer, the technician utilizes the present invention to simultaneously clear the transmission gel and mark the location on the skin that corresponds to the underlying venous anatomy. Since the transmission gel is water soluble and the ink used is water insoluble and quick-drying, the ink mark will remain on the skin even after the remainder of the transmission gel is wiped off at the end of the entire procedure.

The present invention will be an integral facet of the overall strategy to conquer venous diseases. The invention will benefit each of the hospital administrator, the ultrasound technician, and the vascular surgeon. The hospital administrator will benefit from the decreased risk of complications in surgery which, in turn, will increase bed utilization and cut overall hospital costs. In addition, the actual cost of performing the marking procedure will be substantially reduced. The ultrasound technician will benefit from the decrease in the time required to perform the marking procedure. Moreover, only one technician will be needed to perform the procedure. The vascular surgeon will benefit due to the decrease of investigational incisions, the decreased risk of complication, and the decreased total surgery time.

Perhaps the most important attribute of the present invention from a societal viewpoint is the potential for improvement of clinical outcome and the corresponding decrease in hospital stay time. Estimates obtained from the National Center for Health Statistics (1988, Series 13) indicate that the number of surgeries currently carried out in the United States in which the present invention could be utilized totals over 2.1 million. The number is expected to increase. The need for the present invention is apparent.

While the present invention arose in the context of "mapping" the venous anatomy, it is readily apparent to one skilled in the art that the invention is applicable to marking other aspects of the human anatomy, for example, arteries, as well as other internal entities such as tumors.

While the preferred embodiments of the invention and their advantages have been disclosed in the above detailed description, the invention is not limited thereto but only by the spirit and scope of the appended claims.

What is claimed is:

1. A device for cutaneously marking the venous anatomy which comprises:
    a plastic encasing having an orifice;
    a housing inside the plastic encasing having an inlet port and an outlet port;
    a channel inside the housing, the channel connecting the inlet port to the outlet port;
    a propellent source having a pressurized gas contained therein, the propellent source being connected to the inlet port;
    a reservoir having a marking fluid contained therein, the marking fluid coming in contact with the pressurized gas at the orifice;
    a switch connected to the channel, the switch being selectively engageable to allow the pressurized gas to pass through the channel to the outlet port, the pressurized gas coming in contact with the marking fluid at the office;
    a piercing needle; and
    a lever, the piercing needle entering the propellent source upon engagement of the lever and thereby releasing the pressurized gas into the channel.

2. A system for cutaneously marking the anatomy with a marking fluid by means of a propellent source comprising:
    an ultrasound transmission gel to coat the skin corresponding to the anatomy to be marked;
    an ultrasound transducer for manipulation over the transmission gel to pinpoint the portion of the anatomy to be marked; and
    a device which simultaneously clears the transmission gel from the skin corresponding to the portion of the anatomy to be marked as pinpointed by the ultrasound transducer and marks the skin with the marking fluid.

3. A system for cutaneously marking the venous anatomy of a human being with a marking fluid in preparation for surgery comprising:
    an ultrasound transmission gel to coat the skin corresponding to the venous anatomy to be marked;
    an ultrasound transducer for manipulation over the transmission gel to pinpoint the portion of the venous anatomy to be marked; and
    a device which simultaneously clears the transmission gel by means of a propellent source from the skin corresponding to the portion of the venous anatomy to be marked as pinpointed by the ultrasound transducer and marks the skin with the marking fluid.

4. The system as recited in claim 2 or 3, wherein the device comprises:
   a plastic encasing having an orifice;
   a housing inside the plastic encasing having an inlet port and an outlet port;
   a channel inside the housing, the channel connecting the inlet port to the outlet port;
   a propellent source having said pressurized gas contained therein, the propellent source being connected to the inlet port;
   a reservoir having a marking fluid contained therein, the marking fluid coming in contact with the pressurized gas at the orifice; and
   a switch connected to the channel, the switch being selectively engageable to allow the pressurized gas to pass through the channel to the outlet port, the pressurized gas coming in contact with the marking fluid at the orifice.

5. The system as recited in claim 4, wherein the inlet port of the device comprises:
   a piercing needle; and
   a lever, the piercing needle entering the propellent source upon engagement of the lever and thereby releasing the pressurized gas into the channel.

6. The system as recited in claim 4, wherein the channel of the device comprises:
   a first segment;
   a second segment; and
   a regulator made of a porous material with baffles, the first segment connecting the inlet port to the regulator, the second segment connecting the regulator to the outlet port.

7. The system as recited in claim 4, wherein the orifice of the device comprises:
   an opening and the outlet port, the opening allowing the marking fluid to be discharged from the reservoir, the opening and the outlet port positioned so that the pressurized gas and the marking fluid come in contact.

8. The system as recited in claim 7, wherein the opening of the device is positioned at an angle between approximately 30° and approximately 60° to the outlet port.

9. The system as recited in claim 4, wherein the pressurized gas of the device comprises a mixture of between approximately 80% and approximately 90% 1.1-diflouroethane and between approximately 10% and 20% butane by volume.

10. The system as recited in claim 4, wherein the marking fluid of the device comprises an ink combined with between approximately 80% and approximately 92% xylene by weight.

11. The system as recited in claim 2 or 3, wherein the device comprises:
    an aerosol can having a chamber, the chamber containing a mixture of a pressurized gas and a marking fluid;
    a channel inside the chamber connected the chamber to an inlet port; and
    an actuator having a spout connected to the inlet port, the actuator being selectively engageable to allow the mixture to pass through the channel and the inlet port and to discharge through the spout.

12. The system as recited in claim 11, wherein the spout of the device is positioned at an angle between approximately 30° and approximately 60° to the vertical center axis of the aerosol can.

13. The system as recited in claim 11, wherein the pressurized gas of the device comprises a mixture of between approximately 80% and approximately 90% 1.1-diflouroethane and between approximately 10% and 20% butane by volume.

14. The system as recited in claim 11, wherein the marking fluid of the device comprises an ink combined with between approximately 80% and approximately 92% xylene by weight.

* * * * *